United States Patent
Kolb et al.

(10) Patent No.: US 6,951,946 B2
(45) Date of Patent: Oct. 4, 2005

(54) LARGE SCALE SYNTHESIS OF 1,2,4- AND 1,3,4-OXADIAZOLE CARBOXYLATES

(75) Inventors: Hartmuth C. Kolb, San Diego, CA (US); Ramanaiah C. Kanamarlapudi, Bridgewater, NJ (US); Paul F. Richardson, Monmouth Junction, NJ (US)

(73) Assignee: Lexicon Pharmaceuticals, Inc., New Brunswick, NJ (US)

( * ) Notice: Subject to any disclaimer, the term of this patent is extended or adjusted under 35 U.S.C. 154(b) by 19 days.

(21) Appl. No.: 10/391,880

(22) Filed: Mar. 19, 2003

(65) Prior Publication Data

US 2004/0019215 A1 Jan. 29, 2004

Related U.S. Application Data

(60) Provisional application No. 60/365,437, filed on Mar. 19, 2002.

(51) Int. Cl.$^7$ ............................................. C07D 271/06
(52) U.S. Cl. ........................................................ 548/131
(58) Field of Search .......................................... 548/131

(56) References Cited

U.S. PATENT DOCUMENTS 3,367,959 A * 2/1968 Fetscher et al. ............ 560/168

OTHER PUBLICATIONS

Hett et al, Organic Process Research and Development, vol. 6, p. 896–897 (2002).*
Surjono et al, Book of Abstracts, 218$^{th}$ ACS National Meeting, New Orleans, Aug. 22–26 (1999).*
Wei et al, Thermochimica Acta vol. 421, p. 1–9 (2004).*
Borg et al, J. Org. Chem., vol. 60, p. 3112–3120 (1995).*
□□Branco et al, Tetrahedron, vol. 48, No. 30, p. 6335–6360 (1992).*

* cited by examiner

*Primary Examiner*—Bernard Dentz
(74) *Attorney, Agent, or Firm*—McDonnell Boehnen Mulbert & Berghoff

(57) ABSTRACT

Disclosed are efficient and scalable processes for preparing 1,2,4- and 1,3,4-oxadiazole carboxylates from readily available starting materials.

26 Claims, No Drawings

LARGE SCALE SYNTHESIS OF 1,2,4- AND 1,3,4-OXADIAZOLE CARBOXYLATES

This application claims priority from Provisional Application 60/365,437 Mar. 19, 2002.

BACKGROUND OF THE INVENTION

1. Field of the Invention

This invention relates to an efficient and scalable process for preparing 1,2,4- and 1,3,4-oxadiazole carboxylates from readily available starting materials.

2. Description of the Related Art

Oxadiazoles are widely used as ester and amide bioisosteres. They are also useful as antiviral agents, neuroprotectants, and anti-inflammatory agents. An object of the present invention is to develop an efficient, scalable, and cost effective procedure for preparing multigram quantities of 1,2,4- and 1,3,4-oxadiazole carboxylates from readily available starting materials.

1,2,4-Oxadiazoles can be prepared by condensing an amidoxime with an acid chloride or an acid anhydride. A limitation of this method is the availability of the starting amidoxime, which is usually prepared by treating a substituted oximyl chloride the highly toxic and caustic ammonia gas. This method also requires the use of expensive starting materials and cannot be used to generate a wide variety of 1,2,4-oxadiazoles. In addition, this procedure is not readily amenable to large scale synthesis.

1,3,4-Oxadiazoles have been prepared by making a diacylhydrazine and treating it with thionyl chloride and pyridine to form a 1,2,3,4-oxathiadiazole-S-oxide intermediate, which then thermally eliminates sulfur dioxide to yield the desired 1,3,4-oxadiazole. Borg, S., Estenne-Boutou, G., Luthman, K., Csoregh, I., Hesselink, W., U. B. *J. Org. Chem.*, 1995, 60, 2112–2120. This methodology has several drawbacks. First, the procedure is extremely inefficient, affording yields of 6 to 30 percent. Second, it is not amenable to scale up. Finally, this method uses acidic dehydrating agents, which will destroy any acid labile groups. Next, the preparation of the diacylhydrazide requires the use of triethylamine, a very odiferous and relatively expensive base. The method also requires numerous expensive and time consuming chromatographic separations in order to obtain the pure desired product. Finally, many 1,3,4-oxadiazoles are acid labile and readily decompose when attempting to remove the BOC group with HCl.

Another key limitation of the prior art methods for producing the 1,2,4- and 1,3,4-oxadiazoles is that the tertiary-butoxy carbonyl (BOC) nitrogen-protecting group is left intact at the end of the synthesis. BOC groups are normally removed under acidic conditions in a protic solvent, such as dry hydrogen chloride in saturated methanol or trifluoroacetic acid in methanol. If these methods are used to remove the BOC group from the oxadiazole product, decomposition frequently occurs, particularly in the synthesis of 1,3,4-oxadiazole systems. The use of toxic HCl gas is also undesirable.

A safe and efficient procedure for the synthesis of 1,2,4- and 1,3,4-oxadiazoles is desired that is amenable to scale up, that affords increased yields, and that does not require: 1) the use of expensive, sensitive or highly toxic reagents; 2) the need for column chromatography; 3) and the use of harsh deprotection methods.

SUMMARY OF THE INVENTION

This invention provides for efficient, scalable, safe, and cost effective methods for the preparation of 1,2,4- and 1,3,4-oxadiazoles.

Specifically, the present invention provides for a method for preparing 1,2,4-oxadiazoles comprising:

A) reacting a cyanocarboxylate with a hydroxylamine salt in the presence of a first base to form an amidoxime;

B) reacting the amidoxime with an acid anhydride in the presence of a second base to afford a protected 1,2,4-oxadiazole carboxylate; and C) deprotecting the 1,2,4-oxadiazole carboxylate to form the product.

The instant invention also provides a method for preparing 1,3,4-oxadiazoles comprising:

A) reacting an N-protected amino acid ester with hydrazine to form an N-protected acylhydrazide;

B) reacting the N-protected acylhydrazide with a chloro-oxo-acetic acid ester in the presence of a first base to afford an N-protected diacylhydrazide;

C) cyclizing the N-protected diacylhydrazide in the presence of a dehydrating reagent and a second base to afford the N-protected 1,3,4-oxadiazole;

D) deprotecting the N-protected 1,3,4-oxadiazole to form the product.

1,2,4-Oxadiazoles and 1,3,4-oxadiazoles are widely used as ester and amide bioisosteres. They are also useful as antiviral agents, neuroprotectants, and anti-inflammatory agents, or precursors thereof.

DETAILED DESCRIPTION OF THE INVENTION

According to Scheme 1, the present invention relates to a method for the formation of 1,2,4-oxadiazoles (v) by treating an amidoxime (ii) and an anhydride (iv) with a base. The resulting product (v), where $R_2$ is a protecting group, and preferably a BOC protecting group, is then deprotected using hydrogen chloride in ethyl acetate to afford the final product (v) where $R_2$ is hydrogen.

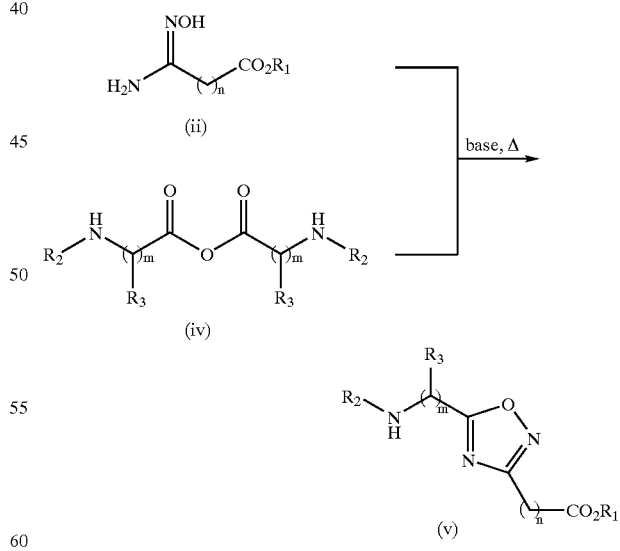

In Scheme 1:

m and n independently are 0 to 6;

$R_1$ is $C_1$–$C_6$ alkyl or arylalkyl, where each aryl is. optionally substituted with one, two or three groups independenly selected from $C_1$–$C_6$ alkyl, $C_1$–$C_6$ alkoxy, halogen, nitro, trifluoromethyl, and trifluoromethoxy; and $R_2$ is a suitable amino acid protecting group; and each $R_3$ is independently selected from hydrogen, a suitably protected amino acid residue, or heterocycloalkyl optionally substituted with $C_1$–$C_6$ alkyl, or $C_1$–$C_6$ alkyl optionally substituted with one or two groups independently selected from thioalkyl, hydroxy, $C_1$–$C_6$ alkoxy, carboxamido, mono or di ($C_1$–$C_6$ alkyl) carboxamido, heterocycloalkyl, amidinyl, mono or di($C_1$–$C_6$)amino, protected amino, protected carboxyl, and phenyl, optionally substituted with one or two groups independently selected from $C_1$–$C_6$ alkoxy and $C_1$–$C_6$ alkyl.

In a preferred embodiment, $R_1$ is $C_1$–$C_6$ alkyl or benzyl, $R_2$ is tertiary-butoxycarbonyl, and $R_3$ is an amino acid residue or $C_1$–$C_6$ alkyl.

The amidoxime (ii) can be purchased or prepared, such as, for example, by treating a cyanocarboxylate (i) with hydroxylamine or a salt thereof, and a base in a solvent, as depicted in Scheme 2.

Scheme 2

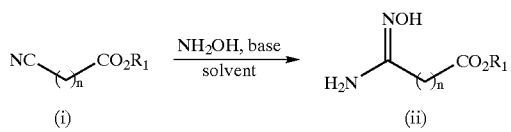

wherein n and $R_1$ are as defined above for Scheme 1.

In preferred embodiment of Scheme 2, the hydroxylamine salt is selected from hydroxylamine hydrochloride, hydroxylamine nitrate, hydroxylamine sulfate, aqueous hydroxylamine, and hydroxylamine phosphate.

Another embodiment of the present invention relates to a method for the formation of 1,3,4-oxadiazoles. Accordingly, a hydrazide (viii) is acylated with an acylating agent and a base in a non-anhydrous solvent to afford the diacylhydrazide (ix). The diacylhydrazide is then cyclized using triphenylphosphine, carbon tetrachloride and a base in a solvent to form the protected 1,3,4-oxadiazoles (x), where $R_2$ is tert-butoxycarbonyl (BOC.) The protected 1,3,4-oxadiazole (x) is then deprotected using hydrogen chloride in ethyl acetate or dioxane.

According to Scheme 3:

z is 1 to 6;

each $R_4$ is independently selected from hydrogen, a suitably protected amino acid residue, or heterocycloalkyl optionally substituted with $C_1$–$C_6$ alkyl, or $C_1$–$C_6$ alkyl optionally substituted with one or two groups independently selected from thioalkyl, hydroxy, $C_1$–$C_6$ alkoxy, carboxamido, mono or di($C_1$–$C_6$ alkyl) carboxamido, heterocycloalkyl, amidinyl, mono or di($C_1$–$C_6$)amino, protected amino, protected carboxyl, and phenyl, optionally substituted with one or two groups independently selected from $C_1$–$C_6$ alkoxy and $C_1$–$C_6$ alkyl;

$R_5$ is $C_1$–$C_6$ alkyl or arylalkyl, where each aryl is optionally substituted with one, two or three groups independently selected from $C_1$–$C_6$ alkyl, $C_1$–$C_6$ alkoxy, halogen, nitro, trifluoromethyl, and trifluoromethoxy; and $R_6$ is a suitable amino acid protecting group.

In a preferred embodiment of Scheme 3, $R_5$ is lower alkyl, and more preferably, a $C_1$–$C_4$ alkyl group. Most preferably, the $C_1$–$C_4$ alkyl group is ethyl.

Examples of acceptable first bases used in the present method are those with alkali metals or alkaline earth metals such as sodium, potassium, calcium and magnesium, and those with organic bases including, but not limited to, amines. Preferred bases are alkali metal bases or alkaline earth metal bases. Even more preferred bases are alkaline metal carbonates, such as, for example, sodium carbonate, potassium carbonate, lithium carbonate, calcium carbonate, and cesium carbonate.

In still yet another preferred embodiment, the cyanocarboxylate is treated with a hydroxylamine salt and a first base at a temperature of from between 0° C. and 75° C. Most preferably, the temperature is about 15° C. to about 30° C.

In another preferred embodiment, the cyanocarboxylate is treated with a hydroxylamine salt and a first base in at least one suitable solvent. More preferably, the solvent is protic, including for example, alcohols, acids, water and mixtures thereof. Even more preferably, the protic solvent is a combination of ethanol and water.

Suitably protected-amino acid and/or amino acid residues of the present invention include, but are not limited to, N-tertiary-butoxycarbonyl glycine, N-tertiary-butoxycarbonyl alanine, N-tertiary-butoxycarbonyl valine, N-tertiary-butoxycarbonyl leucine, N-tertiary- Scheme 3

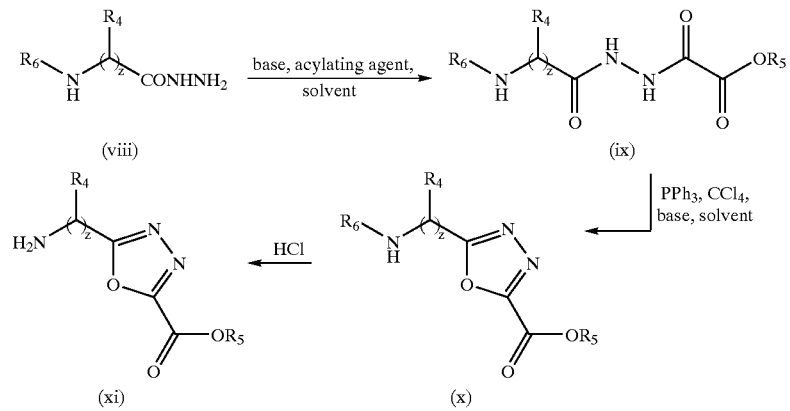

butoxycarbonyl methionine, N-tertiary-butoxycarbonyl isoleucine, N-tertiary-butoxycarbonyl serine, N-tertiary-butoxycarbonyl threonine, N-tertiary-butoxycarbonyl cysteine, N-tertiary-butoxycarbonyl proline, N-tertiary-butoxycarbonyl asparagine, N-tertiary-butoxycarbonyl glutamine, N-tertiary-butoxycarbonyl phenylalanine, N-tertiary-butoxycarbonyl tyrosine, N-tertiary-butoxycarbonyl tryptophan, N-tertiary-butoxycarbonyl lysine, N-tertiary-butoxycarbonyl arginine, N-tertiary-butoxycarbonyl histidine, N-tertiary-butoxycarbonyl aspartine, and N-tertiary-butoxycarbonyl glutamine. It is understood that any such protected-amino acid may have further reactive sidechains. In such instances, the reactive sidechains are also suitably protected.

In still another preferred embodiment, the amidoxime intermediate is treated with the acid anhydride intermediate in the presence of a second base at a temperature of from between 0° C. and 125° C. Even more preferably, the temperature is between 20° C. and 125° C.

The second base is preferably an organic base. More preferably, the organic base is anhydrous. Even more preferably, the anhydrous, organic base is aromatic, including, for example, lutidine, pyridine, collidine and 2,6-di-tertiary-butyl pyridine. Most preferably, the second base is anhydrous pyridine.

In still another preferred embodiment, deprotecting the 1,2,4-oxadiazole carboxylate product by treatment with an appropriate deprotecting agent is performed at a temperature of from between −10° C. and 85° C. More preferably, the temperature is from about 0° C. to about 85° C.

Examples of deprotecting reagents include, but are not limited to, trifluoroacetic acid, acetic acid, hydrogen chloride, hydrogen bromide, hydrogen iodide, triflic acid, and methanesulfonic acid. Preferably, the protic reagent is hydrogen chloride gas. Even more preferably, the protic reagent is hydrogen chloride gas dissolved in either 1,4 dioxane ("dioxane"), ethyl acetate or diethylether.

In another preferred embodiment, the deprotection is carried out in at least one suitable solvent. More preferably, the solvent is aprotic, including for example, ethers, halogenated hydrocarbons, esters and sulfoxides. Even more preferably, the aprotic solvent is ethyl acetate.

In a preferred embodiment, the nitrogen protecting group is acid labile. More preferably, the nitrogen protecting group is tertiary-butoxycarbonyl (BOC.)

In another preferred embodiment, the N-protected acyl-hydrazide is treated with a chloro-oxo-acetic acid ester in the presence of at least one solvent. More preferably, the solvent is aprotic, including for example, ethers, esters and sulfoxides. Even more preferably, the solvent is tetrahydrofuran.

In yet another preferred embodiment, the diacylhydrazide is formed at temperatures between −10° C. and 40° C.

The cyclization of the N-protected diacylhydrazide can also be performed in the presence of at least one solvent. Preferably, the solvent is a halogenated hydrocarbon, including, for example, trichloroethane, methylene chloride, chloroform and carbon tetrachloride. Even more preferably, the solvent is dichloromethane.

Examples of a suitable second base include, but are not limited to, triethylamine, diisopropylethylamine, pyridine, and lutidine. More preferably, the second base is triethylamine.

The cyclization of the N-protected diacylhydrazide can also be performed in the presence of a phosphorous reagent combined with a per-halogenated methane. Preferably, the phosphorous reagent is triphenylphosphine and the perhalogenated methane is carbon tetrachloride.

In another preferred embodiment, the cyclization of the N-protected diacylhydrazide is performed at temperature of about 15° C. to about 90° C.

The N-protected 1,3,4-oxadiazole can be deprotected using reagents such as, for example, trifluoroacetic acid, acetic acid, hydrogen chloride, hydrogen bromide, hydrogen iodide, triflic acid, and methanesulfonic acid. More preferably, the protic reagent is hydrogen chloride gas. Even more preferably, the protic reagent is hydrogen chloride gas dissolved in dioxane, ethyl acetate or diethylether.

In a preferred embodiment, the N-protected 1,3,4-oxadiazole is deprotected in the presence of at least one solvent. More preferably, the solvent is aprotic, including for example, ethers, halogenated hydrocarbons, esters and sulfoxides. Even more preferably, the solvent is ethyl acetate.

In another preferred embodiment, the deprotection of the nitrogen is performed at temperature of about −10° C. to about 15° C.

By "alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. These groups may be substituted with up to four groups mentioned below for aryl.

By "alkyl" in the present invention is meant straight or branched chain alkyl groups having 1–6 carbon atoms, such as, for example, methyl, ethyl, propyl, isopropyl, n-butyl, sec-butyl, iso-butyl, tert-butyl, pentyl, 2-pentyl, isopentyl, neopentyl, hexyl, 2-hexyl, and 3-hexyl.

By "aryl" is meant an aromatic carbocyclic group having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl), which is optionally mono-, di-, or trisubstituted with halogen, —OH, —SH, alkyl, alkoxy, alkylthio, trifluoromethyl, trifluoromethoxy, acyloxy, aryl, heteroaryl, amino, mono-or dialkylamino, and nitro. A preferred aryl group is phenyl.

A "cycloalkyl" group is a nonaromatic cyclic ring or fused rings having from 3 to 7 members. Examples include cyclopropyl, cyclobutyl, and cycloheptyl. These rings may be substituted with one or more of the substituent groups mentioned below for aryl, for example, alkyl, halo, amino, hydroxy, and alkoxy. Typical substituted carbocyclic groups include 2-chlorocyclopropyl; 2,3-diethoxycyclopentyl; and 2,2,4,4-tetrafluorocyclohexyl. The carbocyclic group may contain one or two heteroatoms selected from oxygen, sulfur and nitrogen, and such ring systems may be referred to as "heterocyclic." Examples include pyranyl, tetrahydrofuranyl, and dioxanyl. These heterocyclic groups may be substituted with up to four of the substituent groups mentioned for aryl to gives groups such as 3-chloro-2-dioxanyl, and 3,5-dihydroxymorpholino. In addition, the carbocyclic or heterocyclic group may also contain one or more internal double bonds, as long as having such double bonds does not make the carbocycle or heterocycle aromatic.

The terms "halogen" or "halo" indicate fluorine, chlorine, bromine, and iodine.

The term "heterocycloalkyl," refers to a non-aromatic ring system containing at least one heteroatom selected from nitrogen, oxygen, and sulfur. The heterocycloalkyl ring may be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrolidinyl.

The term "protecting group", "suitably protected" or "nitrogen protecting group," as used herein, refers to groups known in the art that are readily introduced on to and removed from a nitrogen atom. Examples of nitrogen protecting groups include tertiary-butoxy carbonyl (BOC), carbobenzyloxy (Cbz), benzoyl, and benzyl. Other examples of acceptable nitrogen protecting groups are found in "Protective Groups in Organic Synthesis", 3rd Ed., Greene, T. W.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms can be obtained by asymmetric synthesis, using enantiomerically enriched starting materials or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

Scheme 4 depicts an example for the formation of the acid anhydride (iv), which is used in the present invention for the preparation of 1,2,4-oxadiazoles. Specifically, (iv) can be prepared by treating a suitably protected amino acid (iii) with a dehydrating agent in a solvent.

Scheme 4

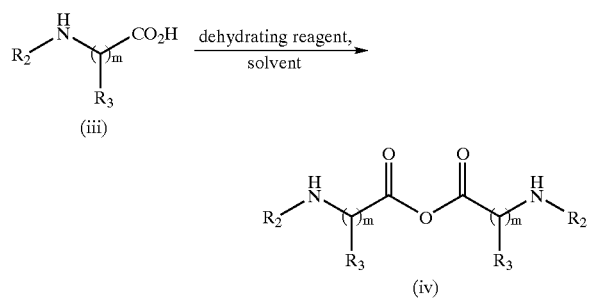

In Scheme 4, $R_2$, $R_3$ and m are as defined above.

Scheme 5 exemplifies the preparation of the protected acyl hydrazide (vii), which is used in the preparation of 1,3,4-oxadiazoles. Using means well known in the art, amino-ester (vi) is treated with a protecting group precursor to form the protected amino-ester (vii), which is then treated with hydrazine to form the acyl hydrazide (viii.)

Scheme 5

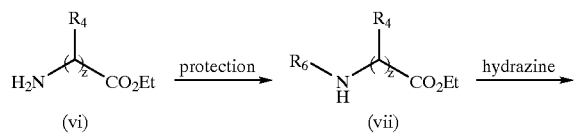

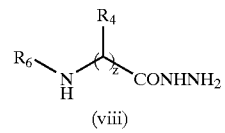

In Scheme 5, z, $R_4$ and $R_6$ are as defined above.

The disclosures in this application of all articles and references, including patents, are incorporated herein by reference.

The invention is illustrated further by the following examples, which are not to be construed as limiting the invention in scope or spirit to the specific procedures described in them.

The starting materials and various intermediates may be obtained from commercial sources, prepared from commercially available organic compounds, or prepared using well-known synthetic methods.

Representative examples of methods for preparing intermediates of the invention are set forth below.

EXAMPLES

Example 1

Synthesis of Anhydrides 1. 3-[(tert-Butoxy)carbonylamino]propanoyl 3-[(tert-butoxy)carbonylamino]propanoate (1a).

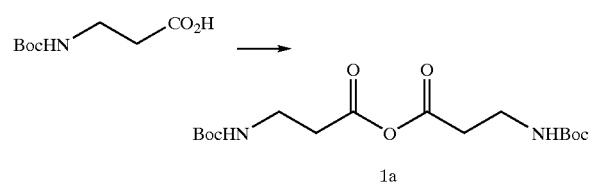

A solution of N, N-dicyclohexylcarbodiimide (DCC) (109 g, 0.529 mol) in dry methylene chloride (200 ml) is added dropwise to a 0° C. solution of BOC protected β-alanine (200 g, 1.058 mol) in dry methylene chloride (800 ml.) After the addition is complete, the reaction mixture is stirred for 2 hours. The resulting N, N-dicyclohexylurea (DCU) is removed via filtration, and the filtrate is concentrated in vacuo to yield the crude anhydride 1a, which is used directly in the next step without further purification.

Example 2

Synthesis of Amidoximes

1. Ethyl 2-amino-2-(hydroxyimino)acetate (2a)

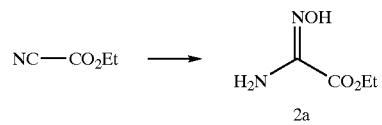

Water (600 ml) is added dropwise over a period of two hours to a vigorously stirred, room temperature mixture of ethyl cyanoformate (99 g, 1 mol), hydroxylamine hydrochloride (105 g, 1.5 mol ) and sodium carbonate (82 g, 0.77 mol ) in ethanol (1 L.) The resulting solution is stirred until the starting material has been consumed. When the reaction is complete, most of the solvent is removed in vacuo and the resulting residue is extracted with methylene chloride (3×200 ml.) The combined organic extracts are washed with brine (250 ml), dried ($Na_2SO_4$), filtered and concentrated to afford 120.1 g (91%) of compound 2a as a white solid. Further purification can be achieved by crystallization from chloroform and hexanes. $^1H$ NMR ($CDCl_3$): δ9.15 (br s, OH), 5.12 (br s, 2H), 4.32 (q, 2H), 1.42 (t, J=7.1 Hz, 3H). $^{13}C$ NMR ($CDCl_3$): δ161.4, 144.4, 62.8, 14.3.

2. Ethyl 3-amino-3-(hydroxyimino)propanoate (2b)

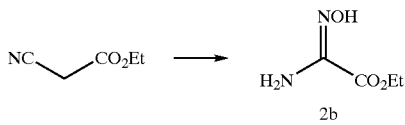

Water (500 ml) is added dropwise over a period of 2 hours to a vigorously stirred, room temperature mixture of ethyl cyanoacetate (100 g, 0.884 mol), hydroxylamine hydrochloride (3 g, 1.328 mol) and sodium carbonate (70 g, 0.66 mol) in ethanol (1 L.) After stirring for an additional 12 hours at room temperature, the reaction mixture is heated to 50° C. for 1 hour. The resulting light red colored solution is allowed to cool to room temperature and then stirred for an additional 2 hours. The solids formed are removed via filtration and the filtrate is concentrated in vacuo. The resulting residue is extracted with methylene chloride (3×200 ml). The combined organic extracts are washed with brine (300 ml), dried ($Na_2SO_4$), filtered and concentrated to afford 85.2 g (66%) of compound 2b as a slightly colored solid. Compound 2b can be further purified by crystallization from chloroform and hexanes. $^1H$ NMR (CDCl3): δ8.45 (br s, 1H), 5.25 (br s, 2H) 4.25(q, 2H), 3.15 (s, 2H), 1.35 (t, J=7 Hz, 3H).

Example 3

Synthesis of 1,2,4-Oxadiazoles

1. Ethyl 5-{2-[(tert-butoxy)carbonylamino]ethyl}-1,2,4-oxadiazole-3-carboxylate (3a)

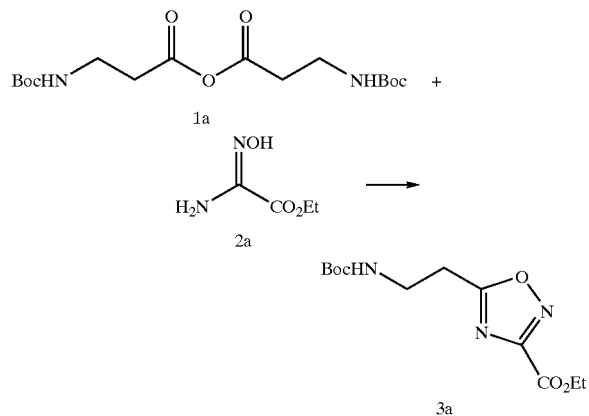

Amidoxime 2a (46.6 g, 0.353 mol) in dry pyridine (100 ml) is added dropwise to a room temperature solution of crude anhydride 1a in dry pyridine (300 ml.) The reaction mixture is then refluxed for 6 hours. During this time, the reaction is monitored by TLC on silica gel using ether/hexanes (2:1) as the eluent. Upon consumption of the starting material, the reaction mixture is cooled to room temperature and then water (200 ml) is added. The solvent is evaporated in vacuo, and the resulting residue is dissolved in methylene chloride (300 ml) and washed sequentially with water (200 ml), saturated sodium bicarbonate (3×100 ml) and brine (100 ml). The organic phase is dried over sodium sulfate, filtered, and concentrated in vacuo to afford the crude product. The crude product is then filtered through a pad of silica gel using hexanes/ether (2:1) as the eluent to afford 71 g (78%) of the pure protected oxadiazole 3a as a white crystalline solid. Further purification can be effected, if desired, by crystallization from chloroform and hexanes. $^1H$ NMR ($CDCl_3$): δ5.21(bs s, 2H), 4.52 (q, 2H), 1.62(d, J=6.94 Hz, 3H), 1.44(m, 12H). $^{13}C$ NMR ($D_2O$): δ182.5, 162.0, 157.8, 155.1, 80.7, 63.3, 44.5, 28.5, 19.9, 14.3.

2. Ethyl 5-(2-aminoethyl)-1,2,4-oxadiazole-3-carboxylate (4a)

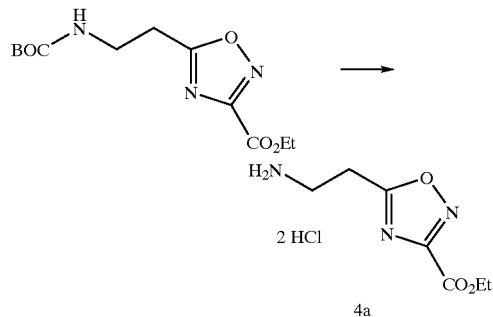

Dry hydrogen chloride gas is bubbled through a 0° C. solution of protected oxadiazole 3a (50 g) in ethyl acetate (750 ml) until a white solid begins to precipitate (approximately 15 minutes.) Then the solution is refluxed for 10 hours, cooled to room temperature, and filtered. The resulting solid is washed with ether and dried to afford 41 g (96%) of compound 4a as a white solid. $^1H$ NMR ($D_2O$): δ4.40 (q, 2H), 3.55 (m, 4H), 1.32 (t, 3H). $^{13}C$ NMR ($D_2O$) δ179.1, 161.8, 158.6, 64.6, 36.2, 24.8, 13.7.

Example 4

Boc Protection

1. Ethyl 2-[(tert-butoxy)carbonylamino]acetate (5)

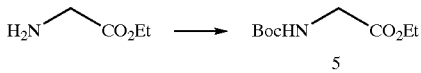

Di-tert-butyl dicarbonate (365 g, 1.67 mol) in tetrahydrofuran (1L) is added dropwise to a 0° C. solution of glycine ethyl ester hydrochloride (232.5 g, 1.66 mol) and triethylamine (497.5 ml, 3.57 mol) in tetrahydrofuran (2.5 L.) The reaction mixture is vigorously stirred for 36 hours and then filtered. The filtrate is the concentrated in vacuo to afford 329.4 9 (98%) of compound 5 as a white solid.

Example 5

Synthesis of Hydrazides

1. Hydrazinocarbonylmethyl-carbamic acid tert-butyl ester(6a)

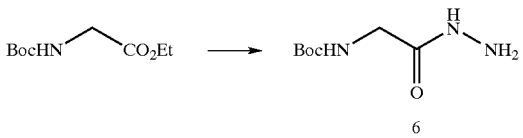

Hydrazine hydrate (222 ml, 6.92 mol) is added dropwise to a room temperature solution of compound 5 (285.7 g, 1.63 mol) in ethanol (500 ml). The initial reaction is mildly exothermic. The reaction is stirred for 36 hours and then the volatiles are removed in vacuo. Water (400 ml) is added to the crude product, briefly stirred, and then removed in vacuo in order to azeotropically remove excess hydrazine. Pentane is added to the resulting white solid, which is broken up by heating gently. After cooling to approximately room temperature, the mixture is filtered and the solid is washed with pentane to afford 236.7 g (90%) of compound 6 as a white solid.

Example 6

Synthesis of Diacylhydrazides

1. Ethyl (N-{2-[(tert-butoxy)carbonylamino]acetylamino}carbamoyl)formate (7)

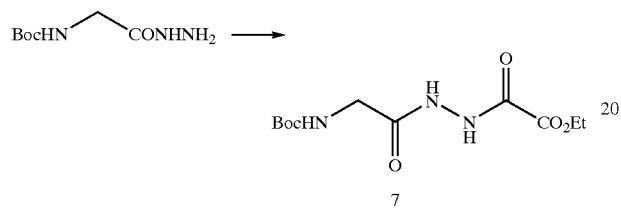

Ethyl oxalyl chloride (81 ml, 0.72 mol) is added dropwise over a period of 90 minutes to a vigorously stirred, 0° C. slurry of compound 6 (136 g, 0.72 mol) and sodium hydrogen carbonate (69 g, 0.82 mol) in tetrahydrofuran (2.5 L.) The reaction mixture is allowed to warm to room temperature and then stirred for an additional 12 hours. The reaction mixture is then filtered through celite and the filtrate is concentrated in vacuo. Toluene (500 ml) is added to the resulting residue, and then volume of solvent is reduced in vacuo to approximately half its original volume. Addition of ethyl ether (1 L) causes some of the product to precipitate as a white solid. The flask is then placed in the freezer overnight. The resulting white solid is collected by vacuum filtration and washed with ethyl ether (500 mL) to afford 114.6 g (55%) of compound 7 as a white solid.

Example 7

Synthesis of 1,3,4-Oxadiazoles

1. Ethyl 5-{[(tert-butoxy)carbonylamino]methyl}-1,3,4-oxadiazole-2-carboxylate (8)

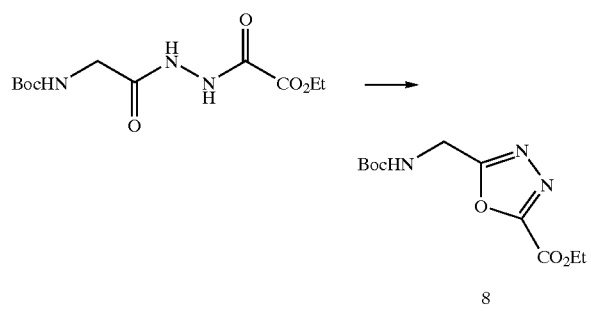

A solution of compound 7 (59 g, 200 mmol) and triethylamine (42 ml, 0.57 mol) in carbon tetrachloride (60 ml) is added to a stirred, room temperature of triphenylphosphine (63 g, 0.24 mol) in methylene chloride (900 ml). The reaction mixture is stirred for 30 minutes and then refluxed for 12 hours. After cooling to room temperature, the volatiles are removed in vacuo and the resulting residue is filtered through silica using methylene chloride:ethyl acetate (9:1) as the eluent. After removing the volatiles in vacuo, the crude product is purified by flash column chromatography over silica gel using methylene chloride:ethyl acetate (19:1) as the eluent. 24 g (44%) Of compound 8 is obtained as orange oil, which solidifies to a yellow solid on standing.

2. Ethyl 5-(aminomethyl)-1,3,4-oxadiazole-2-carboxylate (9)

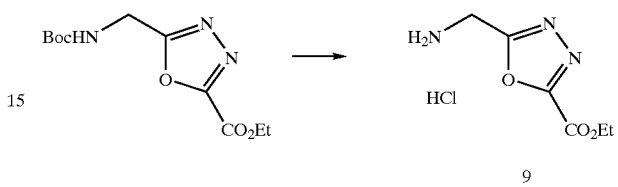

Dry hydrogen chloride gas is bubbled through ethyl acetate (500 ml) at 0° C. for 10 minutes. Compound 8 (40.6 g, 0.15 mol) is then added portionwise over 5 minutes. Vigorous gas evolution is noticed and the solution quickly turns cloudy. After stirring for 2 hours, the white solid is collected by vacuum filtration and washed exhaustively with diethyl ether (1L) to afford 27.2 g (86%) of compound 9. $^1$H NMR (D$_2$O): δ4.56 (s, 2H), 4.40 (q, 2H), 1.28(t, 3H). $^{13}$C NMR (D$_2$O): δ162.9, 158.5, 160.0, 65.2, 34.4, 13.5.

In an alternative procedure, compound 8 (33.3 g, 0.12 mol) is added portionwise to a 0° C. commercially available solution of hydrogen chloride in 1,4-dioxan (Aldrich, 4 M, 750 ml.) Compound 8 slowly dissolves to afford a clear yellow solution. After stirring for approximately 30 minutes, the reaction mixture turns cloudy. The starting material is consumed in about two hours, as determined by TLC on silica using methylene chloride:ethyl acetate (9:1) as the eluent. The reaction mixture is filtered and a colorless solid product is obtained. The solid is washed exhaustively with ether (1L) to afford 19.2 g (76%) of compound 9.

Alternatively, the deprotection can be performed on the crude product from the cyclization step.

Crude, unpurified compound 8 (5 g) is added portionwise to a 0° C. commercially available solution of hydrogen chloride in 1,4-dioxan (Aldrich, 4 M, 35 ml.) Compound 8a slowly dissolves to afford a clear yellow solution. After stirring for approximately 12 hours, the reaction mixture turns cloudy. TLC on silica using methylene chloride:ethyl acetate (9:1) as the eluent shows the starting material has been consumed. The reaction mixture is filtered and a white solid is obtained. The solid is washed exhaustively with ether (50 mL) to afford 266 mg of compound 9.

Example 8

The compounds depicted in Tables 1 and 2 are essentially prepared according to the procedures described above in Examples 1–7.

TABLE 1

1,2,4-oxadiazoles.

| Compound | Amount prepared (grams) Total Yield (%) | NMR Data | Name |
|---|---|---|---|
| 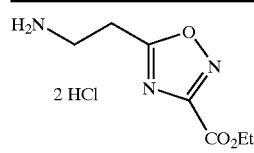 | 107; (87) | $^1$H NMR (D$_2$O) δ 4.40 (q, 2H), 3.55(m, 4H), 1.32(t, 3H). $^{13}$C NMR (D$_2$O): δ 179.1, 161.8, 158.6, 64.6, 36.2, 24.8, 13.7. | 5-(2-Amino-ethyl)-[1,2,4]oxadiazole-3-carboxylic acid ethyl ester dihydro chloride |
| 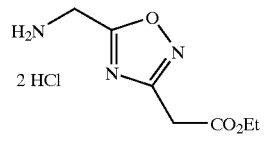 | 107; (78) | $^1$H NMR (D$_2$O) δ 4.65 (s, 2H), 4.25(q, 2H), 3.95(s, 2H), 1.25(t, J=7.1 Hz, 3H). $^{13}$C NMR (D$_2$O): δ 173.7, 170.2, 165.3, 63.4, 35.5, 32.0, 13.7. | (5-Aminomethyl-[1,2,4]oxadiazol-3-yl)-acetic acid ethyl ester dihydro chloride |
| 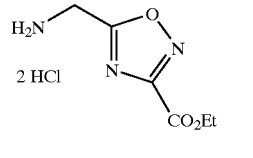 | 85; (82) | $^1$H NMR (D$_2$O) δ 4.65(s, 2H), 4.42(q, 2H), 1.32(t, J=7.3 Hz, 3H). $^{13}$C NMR (D$_2$O): δ 175.0, 162.0, 158.4, 64.7, 35.5, 13.6. | 5-Aminomethyl-[1,2,4]oxadiazole-3-carboxylic acid ethyl ester dihydro chloride |
| 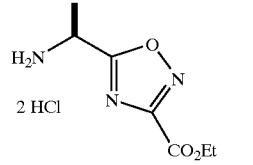 | 50; (76) | $^1$H NMR (D$_2$O) δ 5.05( q, 2H), 4.40(q, 2H), 1.75(d, J=7.06 Hz, 2H), 1.25 (t, J=7.13 Hz, 3H). $^{13}$C NMR (D$_2$O): δ 178.0, 162.0, 158.3, 64.7, 44.3, 16.5, 13.5. | 5-(1-Amino-ethyl)-[1,2,4]oxadiazole-3-carboxylic acid ethyl ester dihydro chloride |

TABLE 2

1,3,4-oxadiazoles prepared using new methodology.

| Compound | Amount prepared (grams); Total Yield (%) | NMR Data | Name |
|---|---|---|---|
| 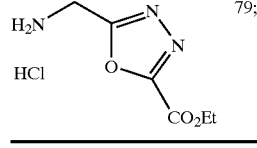 | 79; (22) | $^1$H NMR (D$_2$O) δ 4.56 (s, 2H) , 4.40 (q, 2H), 1.28(t, 3H). $^{13}$C NMR (D$_2$O) δ 162.9, 158.5, 160.0, 65.2, 34.4, 13.5. | 5-Aminomethyl-[1,3,4]oxadiazole-2-carboxylic acid ethyl ester hydro chloride |

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method for preparing a 1,2,4-oxadiazole carboxylate comprising:

A) reacting a cyanocarboxylate with a hydroxylamine salt in the presence of a first base to form an amidoxime;

B) reacting the amidoxime with an acid anhydride in the presence of a second base to afford a protected 1,2,4-oxadiazole carboxylate;

C) deprotecting the 1,2,4-oxadiazole carboxylate to form the product.

2. The method of claim 1 wherein the 1,2,4-oxadiazole carboxylate is

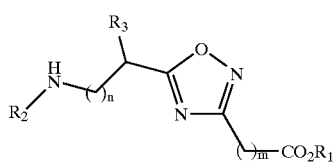

or an acid addition salt thereof; wherein m and n independently are 0 to 6;

R$_1$ is C$_1$–C$_6$ alkyl or arylalkyl, where each aryl is optionally substituted with one, two or three groups independenly selected from $C_1$–$C_6$ alkyl, $C_1$–C6 alkoxy, halogen, nitro, trifluoromethyl, and trifluoromethoxy; and $R_2$ is a suitable amino acid protecting group; and each $R_3$ is independently selected from hydrogen, a suitably protected amino acid residue, or heterocycloalkyl optionally substituted with $C_1$–$C_6$ alkyl, or $C_1$–$C_6$ alkyl optionally substituted with one or two groups independently selected from thioalkyl, hydroxy, $C_1$–$C_6$ alkoxy, carboxamido, mono or di($C_1$–$C_6$ alkyl)carboxamido, heterocycloalkyl, amidinyl, mono or di($C_1$–$C_6$)amino, protected amino, protected carboxyl, and phenyl, optionally substituted with one or two groups independently selected from $C_1$–$C_6$ alkoxy and $C_1$–$C_6$ alkyl.

3. The method of claim 1 wherein the hydroxylamine salt is selected from hydroxylamine hydrochloride, hydroxylamine nitrate; hydroxylamine sulfate, aqueous hydroxylamine, and hydroxylamine phosphate.

4. The method of claim 1 wherein the first base is selected from sodium carbonate, potassium carbonate, lithium carbonate, calcium carbonate, and cesium carbonate.

5. The method of claim 1 wherein the cyanocarboxylate is treated with a hydroxylamine salt and a first base at a temperature of from between 0° C. and 75°C.

6. The method of claim 5 wherein the temperature is about 15° C. to about 30°C.

7. The method of claim 1 wherein the cyanocarboxylate is treated with a hydroxylanuine salt and a first base in at least one suitable solvent.

8. The method of claim 7 wherein at least one solvent is a protic solvent.

9. The method of claim 8 wherein the at least one protic solvent is a combination of ethanol and water.

10. The method of claim 1 wherein the tertiary-butoxycarbonyl protected-amino acid is selected from N-tertiary-butoxycarbonyl glycine, N-tertiary-butoxycarbonyl alanine, N-tertiary-butoxycarbonyl valine, N-tertiary-butoxycarbonyl leucine, N-tertiary-butoxycarbonyl methionine, N-tertiary-butoxycarbonyl isoleucine, N-tertiary-butoxycarbonyl serine, N-tertiary-butoxycarbonyl threonine, N-tertiary-butoxycarbonyl cysteine, N-tertiary-butoxycarbonyl proline, N-tertiary-butoxycarbonyl asparagine, N-tertiary-butoxycarbonyl glutamine, N-tertiary-butoxycarbonyl phenylalanine, N-tertiary-butoxycarbonyl tyrosine, N-tertiary-butoxycarbonyl tryptophan, N-tertiary-butoxycarbonyl lysine, N-tertiary-butoxycarbonyl arginine, N-tertiary-butoxycarbonyl histidine, N-tertiary-butoxycarbonyl aspartine, and N-tertiary-butoxycarbonyl glutamine, wherein if the protected-amino acid has further reactive sidechains, such sidechains are protected with a suitable protecting group.

11. The method of claim 1 wherein the amidoxime intermediate is treated with the acid anhydride intermediate in the presence of a second base to afford the crude 1,2,4-oxadiazole carboxylate product at a temperature of from between 10° C. and 125°C.

12. The method of claim 11 wherein the temperature is between 20° C. and 125°C.

13. The method of claim 1 wherein the second base is an organic base.

14. The method of claim 13 wherein the second base is anhydrous.

15. The method of claim 14 wherein the second base is aromatic.

16. The method of claim 15 wherein the second base is pyridine.

17. The method of claim 1 wherein deprotecting the 1,2,4-oxadiazole carboxylate product by treatment with an appropriate deprotecting agent is performed at a temperature of from between –10° C. and 85°C.

18. The method of claim 17 wherein the reagents are combined at a temperature of about 0° C. and the resulting reaction mixture is heated to about 85°C.

19. The method of claim 1 wherein the deprotecting agent is a protic reagent.

20. The method of claim 19 wherein the protic reagent is hydrogen chloride gas.

21. The method of claim 19 wherein the protic reagent is hydrogen chloride gas dissolved in either 1,4 dioxane or ethyl acetate.

22. The method of claim 1 wherein the deprotection is carried out in at least one suitable solvent.

23. The method of claim 22 wherein the solvent is aprotic.

24. The method of claim 23 wherein the solvent is ethyl acetate.

25. A method for preparing compounds of the formula:

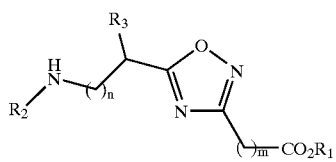

or an acid addition salt thereof; wherein m and n independently are 0 to 6;

$R_1$ is $C_1$–$C_6$ alkyl or arylalkyl, where each aryl is optionally substituted with one, two or three groups independenly selected from $C_1$–$C_6$ alkyl, $C_1$–$C_6$ alkoxy, halogen, nitro, trifluoromethyl, and trifluoromethoxy; and $R_2$ is a suitable amino acid protecting group; and each $R_3$ is independently selected from hydrogen, a suitably protected amino acid residue, or heterocycloalkyl optionally substituted with $C_1$–$C_6$ alkyl, or $C_1$–$C_6$ alkyl optionally substituted with one or two groups independently selected from thioalkyl, hydroxy, $C_1$–$C_6$ alkoxy, carboxamido, mono or di($C_1$–$C_6$ alkyl)carboxamido, heterocycloalkyl, amidinyl, mono or di($C_1$–$C_6$)amino, protected amino, protected carboxyl, and phenyl, optionally substituted with one or two groups independently selected from $C_1$–$C_6$ alkoxy and $C_1$–$C_6$ alkyl;

the method comprising:

A) reacting an intermediate of the structure

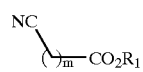

wherein $R_1$ and m are as defined above, with a hydroxyl amine in the presence of a first base and isolating an amidoxime intermediate of the formula:

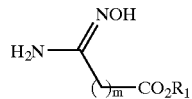

wherein $R_1$ and m are as defined above;

B) reacting the amidoxime intermediate with an acid anhydride of the formula:

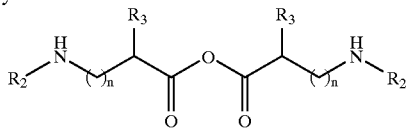

wherein n, $R_2$ and $R_3$ are as defined above, in the presence of a second base and isolating the protected 1,2,4-oxadiazole carboxylate product of the formula:

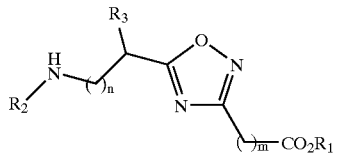

wherein m, n, $R_1$ and $R_3$ are as defined above and $R_2$ is an amino protecting group;

C) reacting the 1,2,4-oxadiazole carboxylate with an acid and isolating the deprotected 1,2,4-oxadiazole carboxylate as an acid addition salt.

26. The method of claim 25 wherein
$R_1$ is $C_1$–$C_6$ alkyl;
$R_2$ is tertiary-butoxycarbonyl or hydrogen; and
$R_3$ is hydrogen or $C_1$–$C_6$ alkyl.

* * * * *